US011939590B1

(12) United States Patent
High et al.

(10) Patent No.: US 11,939,590 B1
(45) Date of Patent: *Mar. 26, 2024

(54) AAV VECTOR COMPOSITIONS AND METHODS FOR GENE TRANSFER TO CELLS, ORGANS AND TISSUES

(71) Applicant: The Children's Hospital of Philadelphia, Philadelphia, PA (US)

(72) Inventors: Katherine A. High, Merion Station, PA (US); Federico Mingozzi, Philadelphia, PA (US); Junwei Sun, Philadelphia, PA (US); Philip Johnson, Wynnewood, PA (US)

(73) Assignee: THE CHILDEN'S HOSPITAL OF PHILADELPHIA, Philadelphia, PA (US)

( * ) Notice: Subject to any disclaimer, the term of this patent is extended or adjusted under 35 U.S.C. 154(b) by 649 days.

This patent is subject to a terminal disclaimer.

(21) Appl. No.: 16/045,619

(22) Filed: Jul. 25, 2018

Related U.S. Application Data

(63) Continuation of application No. 14/378,886, filed as application No. PCT/US2013/026695 on Feb. 19, 2013, now abandoned.

(60) Provisional application No. 61/600,415, filed on Feb. 17, 2012.

(51) Int. Cl.
*A61K 48/00* (2006.01)
*A61K 38/36* (2006.01)
*C12N 15/12* (2006.01)
*C12N 15/86* (2006.01)
*C12N 15/864* (2006.01)

(52) U.S. Cl.
CPC .... *C12N 15/86* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,156,303 A | 12/2000 | Russell et al. | |
| 6,468,524 B1 | 10/2002 | Chiorini et al. | |
| 11,110,153 B2* | 9/2021 | High | C12N 9/644 |
| 2009/0197338 A1 | 8/2009 | Vandenberghe et al. | |
| 2011/0263027 A1 | 10/2011 | Gao et al. | |
| 2012/0128635 A1* | 5/2012 | Gregory | A61P 43/00 435/254.11 |
| 2014/0323956 A1 | 10/2014 | Mendell et al. | |

FOREIGN PATENT DOCUMENTS

| | | |
|---|---|---|
| CN | 102220376 | 10/2011 |
| CN | 101203613 B | 12/2012 |
| WO | 2006/110689 A2 | 10/2006 |
| WO | 2007/120542 A1 | 10/2011 |
| WO | 2011/133890 A2 | 10/2011 |

OTHER PUBLICATIONS

Aravalli et al, Liver-Targeted Gene Therapy: Approaches and Challenges, Liver Transplantation 21:718-737, 2015.*
Geng et al, Efficient Attenuation of NK Cell-Mediated Liver Injury through Genetically Manipulating Multiple Immunogenes by Using a Liver-Directed Vector, J Immunol 2013; 190:4821-4829.*
De Galarreta, Therapeutic editing of hepatocyte genome in vivo, Journal of Hepatology 2017 vol. 67 pp. 818-828.*
Mingozzi and High, Immune responses to AAV vectors: overcoming barriers to successful gene therapy, Blood. 2013, 122(1):23-36.*
Raj et al, Self-complementary adeno-associated viral vectors for gene therapy of hemophilia B: progress and challenges. Expert Rev Hematol., Oct. 2011, pp. 1-19.*
Chirmule, N. et al., Humoral Immunity to Adeno-Associated Virus Type 2 Vectors Following Administration to Murine and Nonhuman Primate Muscle, Journal of Virology, 2000, 74(5):2420-2425.
Daya, S., et al., Gene Therapy Using Adeno-Associated Virus Vectors, Clinical Microbiology Reviews, 2008, pp. 583-593.
Fumoto, S., et al., Targeted Gene Delivery: Importance of Administration Routes, Intech, 2013, pp. 3-31.
Gao, G., et al., Clades of Adeno-Associated Viruses are Widely Disseminated in Human Tissues, Journal of Virology, 2004, 78(12):6381-6388.
Guo, H.H., et al., Protein tolerance to random amino acid change, PNAS, 2004, 101(25):9205-9210.
Herzog, R.W., et al., Long-Term Correction of Canine Hemophilia B by Gene Transfer of Blood Coagulation Factor IX Mediated by Adeno-Associated Viral Vector, Nature Medicine, 1999, (5(1):56-63.
Katz, M.G., et al., Cardiac Gene Therapy: Optimization of Gene Delivery Techniques In Vivo, Human Gene Therapy, 2010, 21:371-380.
Kattenhorn, L.M., et al., Adena-Associated Virus Gene Therapy for Liver Disease, Human Gene Therapy, 2016, 27(12):947-961.
Kim, Y., II, et al, Intratumoral versus Intravenous Gene Therapy Using a Transcriptionally Targeted Viral Vector in an Orthotopic Hepatocellular Carcinoma Rat Model, J. Vasc. Interv. Radiol., 2012; 23(5):704-711.
Lesk, A.M., et al., Prediction of Protein Function from Protein Sequence and Structure, p. 27 and 28, downloaded Sep. 16, 2007.
Martin, P.T., et al., Overexpression of Galgt2 in skeletal muscle prevents injury resulting from eccentric contrations in both mdx and wild-type mice, Am. J. Physiol. Cell Physiol, 2009, 296(3):C476-C488.

(Continued)

Primary Examiner — Maria Marvich
(74) Attorney, Agent, or Firm — Robert M. Bedgood; Pillsbury Winthrop Shaw Pittman LLP

(57) ABSTRACT

The invention relates to adeno-associated virus (AAV) serotype AAV-Rh74 and related AAV vectors, and AAV-Rh74 and related AAV vector mediated gene transfer methods and uses. In particular, AAV-Rh74 targets polynucleotides to cells, tissues or organs for expression (transcription) of genes encoding therapeutic proteins and peptides, and polynucleotides that function as or are transcribed into inhibitory nucleic acid sequences.

19 Claims, 5 Drawing Sheets

Specification includes a Sequence Listing.

(56) References Cited

OTHER PUBLICATIONS

Wright, JF, Manufacturing and characterizing AAV-based vectors for use in clinical studies, Gene Therapy (2008) 15, 840-848.
Xiao, W., et al., Gene therapy vectors based on adeno-associated virus type 1, J Virol. May 1999, 73(5):3994-4003.

* cited by examiner

Figure 3A (SEQ ID NOs:1-4)

Rh74 VP1 Amino Acid (SEQ ID NO:1):
MAADGYLPDWLEDNLSEGIREWWDLKPGAPKPKANQQKQDNGRGLVLPGYKYLGPFNGLDK
GEPVNAADAAALEHDKAYDQQLQAGDNPYLRYNHADAEFQERLQEDTSFGGNLGRAVFQAK
KRVLEPLGLVESPVKTAPGKKRPVEPSPQRSPDSSTGIGKKGQQPAKKRLNFGQTGDSESVPDPQ
PIGEPPAGPSGLGSGTMAAGGGAPMADNNEGADGVGSSSGNWHCDSTWLGDRVITTSTRTWAL
PTYNNHLYKQISNGTSGGSTNDNTYFGYSTPWGYFDFNRFHCHFSPRDWQRLINNNWGFRPKR
LNFKLFNIQVKEVTQNEGTKTIANNLTSTIQVFTDSEYQLPYVLGSAHQGCLPPFPADVFMIPQY
GYLTLNNGSQAVGRSSFYCLEYFPSQMLRTGNNFEFSYNFEDVPFHSSYAHSQSLDRLMNPLIDQ
YLYYLSRTQSTGGTAGTQQLLFSQAGPNNMSAQAKNWLPGPCYRQQRVSTTLSQNNNSNFAW
TGATKYHLNGRDSLVNPGVAMATHKDDEERFFPSSGVLMFGKQGAGKDNVDYSSVMLTSEEEI
KTTNPVATEQYGVVADNLQQQNAAPIVGAVNSQGALPGMVWQNRDVYLQGPIWAKIPHTDGN
FHPSPLMGGFGLKHPPPQILIKNTPVPADPPTTFNQAKLASFITQYSTGQVSVEIEWELQKENSKR
WNPEIQYTSNYYKSTNVDFAVNTEGTYSEPRPIGTRYLTRNL.

Rh74 VP1 DNA (SEQ ID NO:2):
ATGGCTGCCGATGGTTATCTTCCAGATTGGCTCGAGGACAACCTCTCTGAGGGCATTCGCGA
GTGGTGGGACCTGAAACCTGGAGCCCCGAAACCCAAAGCCAACCAGCAAAAGCAGGACAA
CGGCCGGGGTCTGGTGCTTCCTGGCTACAAGTACCTCGGACCCTTCAACGGACTCGACAAGG
GGGAGCCCGTCAACGCGGCGGACGCAGCGGCCCTCGAGCACGACAAGGCCTACGACCAGC
AGCTCCAAGCGGGTGACAATCCGTACCTGCGGTATAATCACGCCGACGCCGAGTTTCAGGA
GCGTCTGCAAGAAGATACGTCTTTTGGGGGCAACCTCGGGCGCGCAGTCTTCCAGGCCAAA
AAGCGGGTTCTCGAACCTCTGGGCCTGGTTGAATCGCCGGTTAAGACGGCTCCTGGAAAGA
AGAGACCGGTAGAGCCATCACCCCAGCGCTCTCCAGACTCCTCTACGGGCATCGGCAAGAA
AGGCCAGCAGCCCGCAAAAAAGAGACTCAATTTTGGGCAGACTGGCGACTCAGAGTCAGTC
CCCGACCCTCAACCAATCGGAGAACCACCAGCAGGCCCCTCTGGTCTGGGATCTGGTACAA
TGGCTGCAGGCGGTGGCGCTCCAATGGCAGACAATAACGAAGGCGCCGACGGAGTGGGTA
GTTCCTCAGGAAATTGGCATTGCGATTCCACATGGCTGGGCGACAGAGTCATCACCACCAGC
ACCCGCACCTGGGCCCTGCCCACCTACAACAACCACCTCTACAAGCAAATCTCCAACGGGA
CCTCGGGAGGAAGCACCAACGACAACACCTACTTCGGCTACAGCACCCCCTGGGGGTATTT
TGACTTCAACAGATTCCACTGCCACTTTTCACCACGTGACTGGCAGCGACTCATCAACAACA
ACTGGGGATTCCGGCCCAAGAGGCTCAACTTCAAGCTCTTCAACATCCAAGTCAAGGAGGT
CACGCAGAATGAAGGCACCAAGACCATCGCCAATAACCTTACCAGCACGATTCAGGTCTTT
ACGGACTCGGAATACCAGCTCCCGTACGTGCTCGGCTCGGCGCACCAGGGCTGCCTGCCTCC
GTTCCCGGCGGACGTCTTCATGATTCCTCAGTACGGGTACCTGACTCTGAACAATGGCAGTC
AGGCTGTGGGCCGGTCGTCCTTCTACTGCCTGGAGTACTTTCCTTCTCAAATGCTGAGAACG
GGCAACAACTTTGAATTCAGCTACAACTTCGAGGACGTGCCCTTCCACAGCAGCTACGCGCA
CAGCCAGAGCCTGGACCGGCTGATGAACCCTCTCATCGACCAGTACTTGTACTACCTGTCCC
GGACTCAAAGCACGGGCGGTACTGCAGGAACTCAGCAGTTGCTATTTTCTCAGGCCGGGCC
TAACAACATGTCGGCTCAGGCCAAGAACTGGCTACCCGGTCCCTGCTACCGGCAGCAACGC
GTCTCCACGACACTGTCGCAGAACAACAACAGCAACTTTGCCTGGACGGGTGCCACCAAGT
ATCATCTGAATGGCAGAGACTCTCTGGTGAATCCTGGCGTTGCCATGGCTACCCACAAGGAC
GACGAAGAGCGATTTTTTCCATCCAGCGGAGTCTTAATGTTTGGGAAACAGGGAGCTGGAA
AAGACAACGTGGACTATAGCAGCGTGATGCTAACCAGCGAGGAAGAAATAAAGACCACCA
ACCCAGTGGCCACAGAACAGTACGGCGTGGTGGCCGATAACCTGCAACAGCAAAACGCCGC
TCCTATTGTAGGGGCCGTCAATAGTCAAGGAGCCTTACCTGGCATGGTGTGGCAGAACCGG
GACGTGTACCTGCAGGGTCCCATCTGGGCCAAGATTCCTCATACGGACGGCAACTTTCATCC
CTCGCCGCTGATGGGAGGCTTTGGACTGAAGCATCCGCCTCCTCAGATCCTGATTAAAAACA
CACCTGTTCCCGCGGATCCTCCGACCACCTTCAATCAGGCCAAGCTGGCTTCTTTCATCACG
CAGTACAGTACCGGCCAGGTCAGCGTGGAGATCGAGTGGGAGCTGCAGAAGGAGAACAGC
AAACGCTGGAACCCAGAGATTCAGTACACTTCCAACTACTACAAATCTACAAATGTGGACTT
TGCTGTCAATACTGAGGGTACTTATTCCGAGCCTCGCCCCATTGGCACCCGTTACCTCACCC
GTAATCTGTAA

Figure 3B

Rh74 VP2 Amino Acid (SEQ ID NO:3):

TAPGKKRPVEPSPQRSPDSSTGIGKKGQQPAKKRLNFGQTGDSESVPDPQPIGEPPAGPSGLGSGTMAAGGGAPMAD
NNEGADGVGSSSGNWHCDSTWLGDRVITTSTRTWALPTYNNHLYKQISNGTSGGSTNDNTYFGYSTPWGYFDFNRFH
CHFSPRDWQRLINNNWGFRPKRLNFKLFNIQVKEVTQNEGTKTIANNLTSTIQVFTDSEYQLPYVLGSAHQGCLPPF
PADVFMIPQYGYLTLNNGSQAVGRSSFYCLEYFPSQMLRTGNNFEFSYNFEDVPFHSSYAHSQSLDRLMNPLIDQYL
YYLSRTQSTGGTAGTQQLLFSQAGPNNMSAQAKNWLPGPCYRQQRVSTTLSQNNNSNFAWTGATKYHLNGRDSLVNP
GVAMATHKDDEERFFPSSGVLMFGKQGAGKDNVDYSSVMLTSEEEIKTTNPVATEQYGVVADNLQQQNAAPIVGAVN
SQGALPGMVWQNRDVYLQGPIWAKIPHTDGNFHPSPLMGGFGLKHPPPQILIKNTPVPADPPTTFNQAKLASFITQY
STGQVSVEIEWELQKENSKRWNPEIQYTSNYYKSTNVDFAVNTEGTYSEPRPIGTRYLTRNL

Rh74 VP3 Amino Acid (SEQ ID NO:4):

MAAGGGAPMADNNEGADGVGSSSGNWHCDSTWLGDRVITTSTRTWALPTYNNHLYKQISNGTSGGSTNDNTYFGYST
PWGYFDFNRFHCHFSPRDWQRLINNNWGFRPKRLNFKLFNIQVKEVTQNEGTKTIANNLTSTIQVFTDSEYQLPYVL
GSAHQGCLPPFPADVFMIPQYGYLTLNNGSQAVGRSSFYCLEYFPSQMLRTGNNFEFSYNFEDVPFHSSYAHSQSLD
RLMNPLIDQYLYYLSRTQSTGGTAGTQQLLFSQAGPNNMSAQAKNWLPGPCYRQQRVSTTLSQNNNSNFAWTGATKY
HLNGRDSLVNPGVAMATHKDDEERFFPSSGVLMFGKQGAGKDNVDYSSVMLTSEEEIKTTNPVATEQYGVVADNLQQ
QNAAPIVGAVNSQGALPGMVWQNRDVYLQGPIWAKIPHTDGNFHPSPLMGGFGLKHPPPQILIKNTPVPADPPTTFN
QAKLASFITQYSTGQVSVEIEWELQKENSKRWNPEIQYTSNYYKSTNVDFAVNTEGTYSEPRPIGTRYLTRNL

AAV VECTOR COMPOSITIONS AND METHODS FOR GENE TRANSFER TO CELLS, ORGANS AND TISSUES

RELATED APPLICATION INFORMATION

This application is a continuation application of U.S. application Ser. No. 14/378,886, filed Aug. 14, 2014, now abandoned, which is the National Phase of International Application No. PCT/US2013/026695, filed Feb. 19, 2013, which designated the U.S. and that International Application was published under PCT Article 21(2) in English, which claims priority to Application Ser. No. 61/600,415, filed Feb. 17, 2012, all of which applications are expressly incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 25, 2018, is named CHOP_0460932_ST25.txt and is 19.2 KB in size.

INTRODUCTION

Genetic disorders, caused by absence or a defect in a desirable gene (loss of function) or expression of an undesirable or defective gene or (gain of function) lead to a variety of diseases. One example of a loss of function genetic disorder is hemophilia, an inherited bleeding disorder caused by deficiency in either coagulation factor VIII (FVIII, hemophilia A) or factor IX (FIX, hemophilia B). One example of a gain of function genetic disorder is Huntington's disease, a disease caused by a pathologic "HTT" gene (encodes the huntingtin protein) that encodes a mutated protein that accumulates within and leads to gradual destruction of neurons, particularly in the basal ganglia and the cerebral cortex.

Current treatment for hemophilia consists in the intravenous administration of recombinant clotting factor either on demand, in case a bleeding occurs, or prophylactically. However, this therapeutic approach has several drawbacks such as the need for repeated infusions, the cost of the treatment, the risk of developing anti-therapeutic factor immune responses, and the risk of potentially fatal bleedings. These limitations have prompted the development of gene-based therapies for hemophilia. To this end, hemophilia is ideal for gene transfer based therapy as 1) the therapeutic window is very wide, as levels just above 1% of normal already can result in a change in phenotype from severe to moderate, and levels of 100% are not associated to any side effects; 2) tissue specific expression of the therapeutic transgene is not strictly required; and 3) there is a considerable experience in measuring the endpoints of therapeutic efficacy. Furthermore, liver expression of clotting factor has been demonstrated to induce immunological tolerance to the clotting factor itself, reducing the likelihood of potentially harmful immune responses against clotting factor.

Currently, adeno-associated virus (AAV) vectors are recognized as the gene transfer vectors of choice since they have the best safety and efficacy profile for the delivery of genes in vivo. Of the AAV serotypes isolated so far, AAV2 and AAV8 have been used to target the liver of humans affected by severe hemophilia B. Both vectors worked efficiently and in the case of AAV8 long-term expression of the therapeutic transgene was documented. Recent data in humans showed that targeting the liver with an AAV vector achieves long-term expression of the FIX transgene at therapeutic levels.

While these data are promising, the identification of AAV serotypes with high tropism for liver and low seroprevalence in humans (a natural host for wild type AAV) is fundamental for 1) achieving therapeutic levels of transgene expression in liver at the lowest vector dose possible to decrease risk of triggering anti-AAV capsid immune responses; and 2) alternate AAV serotypes with unique seroprevalence will allow to treat those patients populations otherwise not eligible for AAV gene transfer due to pre-existing humoral immunity to AAVs. The invention addresses these needs and provides additional benefits.

SUMMARY

The invention provides adeno-associated virus (AAV) serotype AAV-Rh74 vector, and related AAV vectors. Such vectors include AAV-Rh74 which target hepatocyte cells of the liver, among other cell types. As a vector for polynucleotide sequence delivery, AAV-Rh74 and related AAV vectors drive expression of the polynucleotide in cells. Polynucleotides that encode proteins, such as proteins for therapeutic applications are able to be expressed at therapeutic levels after administration. Furthermore, AAV-Rh74 and related AAV vector mediated polynucleotide transfer produced protein expression levels that were significantly higher than several other serotypes currently studied in preclinical and clinical settings (see, e.g., FIGS. 1 and 2). In particular, AAV-Rh74 could target polynucleotides to the liver with efficiency at least comparable or superior to the gold standard for liver transduction, AAV8, both in mice and in hemophilia B dogs. Thus, AAV-Rh74 can be used to deliver polynucleotides, such as gene coding sequences, to express proteins that provide a desirable or therapeutic benefit, as well as for inhibitory nucleotides that reduce or inhibit expression of an undesirable or defective gene, thereby treating a variety of diseases. For example, AAV-Rh74 can be used to deliver therapeutic genes (e.g., FIX, FVIII) to treat hemophilia A, B, and to deliver genes for a wide range of other metabolic or plasma protein deficiencies, or to deliver genes for other therapeutic purposes, such as but not limited to genes encoding zinc finger nucleases to carry out genome editing in the liver, and for local (liver) delivery of immunomodulatory agents such as alpha-interferon for treatment of hepatitis virus infections, or to treat virtually any disease that requires either liver transduction or presence of the therapeutic transgene product in the bloodstream (which can be achieved by targeting the transgenes for liver expression).

In addition to efficient delivery of polynucleotides by AAV-Rh74 and related vectors into cells in vitro, ex vivo and in vivo, prevalence of anti-AAV-Rh74 antibodies in humans is lower than anti-AAV2 antibodies, and differs from that of anti-AAV8 antibodies (Table 1). Owing to low seroprevalence, AAV-Rh74 and related vectors can be used in a greater percentage of humans which otherwise would not be eligible for gene transfer, for example, humans that may be seropositive for other AAV serotypes (e.g., AAV1, AAV2, AAV3, AAV4, AAV5, AAV6, AAV7, AAV8, AAV9, AAV10, AAV11, etc.). In addition, AAV-Rh74 can be efficiently produced at high titers (Table 2). Thus, AAV-Rh74 and related vectors can be produced in large amounts for more prevalent clinical diseases.

In accordance with the invention, there are provided methods for delivering or transferring a heterologous polynucleotide sequence into a mammal or a cell of a mammal. In one embodiment, a method includes administering an adeno-associated virus (AAV) vector that includes a heterologous polynucleotide sequence to a mammal or a cell of a mammal under suitable conditions to deliver or transfer the heterologous polynucleotide sequence into the mammal or the cell of a mammal, thereby delivering or transferring the heterologous polynucleotide. In one aspect, the method allows transfer/delivery of the heterologous polynucleotide into the mammal and/or cell. In another aspect, the method allows transfer/delivery of the heterologous polynucleotide into the mammal and/or cell, and subsequent transcription of the heterologous polynucleotide thereby forming a transcript. In a further aspect, the method allows transfer/delivery of the heterologous polynucleotide into the cell, subsequent transcription to form a transcript and subsequent translation to form a gene product (protein). In particular, for example, in the latter two aspects a heterologous polynucleotide sequence is operably linked to an expression control element conferring transcription of the heterologous polynucleotide sequence, and optionally subsequent translation of the transcript.

DESCRIPTION OF DRAWINGS

FIGS. 3A-3B show AAV-Rh74 VP1, VP2, and VP3 amino acid sequences and, for VP1, polynucleotide (DNA) sequence (SEQ ID NOs:1-4).

DETAILED DESCRIPTION

Figure 1:
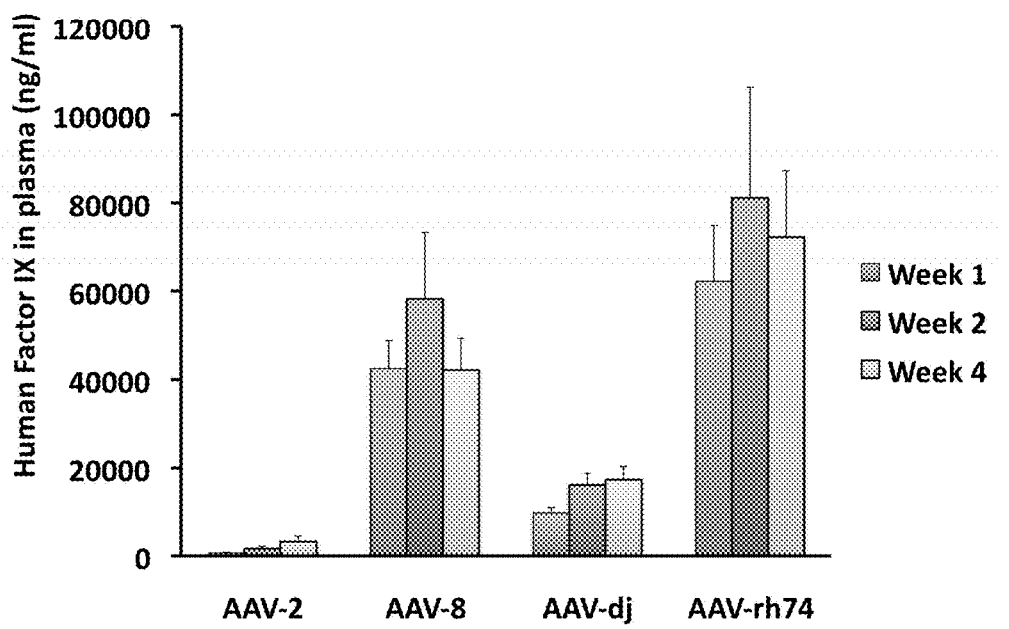
FIG. 1 shows human factor IX (FIX) plasma levels in C57BL/6 mice (n=5 per group) injected via the tail vein with AAV vectors expressing the FIX transgene under the control of a liver-specific promoter. Vector dose $2.5^{10}$ vector genomes per mouse. FIX transgene product (FIX protein) plasma levels were measured by ELISA at weeks 1, 2, and 4 post gene transfer. AAV-Rh74 conferred the highest levels of FIX transgene expression.

The invention is based, at least in part, on data indicating that adeno-associated virus (AAV) serotype AAV-Rh74 has a high tropism for hepatocytes, which are cells of the liver. As a vector for polynucleotide (e.g. genes, inhibitory nucleic acid, etc.) transfer/delivery into cells, AAV-Rh74 can drive therapeutic levels of expression in liver after intravenous administration. Furthermore, AAV-Rh74 mediated gene transfer/delivery produced protein expression levels that were significantly higher than several other serotypes (see, e.g., FIGS. 1 and 2). In particular, AAV-Rh74 targets genes for delivery to the liver with efficiency at least comparable or superior to the gold standard for liver transduction, AAV8, both in mice and in hemophilia B dogs. Thus, AAV-Rh74 can be used to transfer/deliver polynucleotides, such as coding sequences (genes) for proteins that provide a desirable or therapeutic benefit, as well as inhibitory (e.g., anti-sense) nucleic acid that reduce or inhibit expression of an undesirable or defective (e.g., pathologic) gene, thereby treating a variety of diseases. For example, AAV-Rh74 can be used to transfer/deliver therapeutic genes to treat hemophilia A, B, and to transfer/deliver genes for a wide range of other metabolic or plasma protein deficiencies, or for other therapeutic purposes, such as but not limited to genes encoding zinc finger nucleases to carry out genome editing in the liver, and for local (liver) delivery of immunomodulatory agents such as alpha-interferon for treatment of hepatitis virus infections, and to treat virtually any disease that requires either liver transduction or presence of the therapeutic transgene product in the bloodstream (which can be achieved by targeting the transgenes for liver expression).

As set forth herein, adeno-associated virus (AAV) serotype AAV-Rh74 and related AAV vectors provide delivery of polynucleotide sequences to cells ex vivo, in vitro and in vivo. Such polynucleotide sequences can encode proteins such that the cells into which the polynucleotides are delivered express the encoded proteins. For example, AAV-Rh74 and related AAV vectors can include polynucleotides encoding a desired protein or peptide, or a polynucleotide that when transcribed comprises an inhibitory sequence (e.g., RNA), for example, a sequence that targets a gene for inhibition of expression. Vector delivery or administration to a subject (e.g., mammal) therefore provides not only polynucleotides encoding proteins and peptides to the subject, but also inhibitory nucleic acids that target genes for inhibition of expression or function in the subject.

Thus, in accordance with the invention adeno-associated virus (AAV) serotype AAV-Rh74, and related AAV vectors, including polynucleotide sequences encoding peptides and proteins, as well as polynucleotide sequences which directly or when transcribed comprise inhibitory nucleic acids that target genes for inhibition of expression or function, are provided. Such AAV-Rh74 and related AAV vector serotypes (e.g., VP1, VP2, and/or VP3 sequences) are distinct from other AAV serotypes, including, for example, AAV1-AAV11 or Rh10 (e.g., distinct from VP1, VP2, and/or VP3 sequences of any of AAV1-AAV11, or Rh10 serotypes).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes).

AAV-Rh74 has gene/protein sequences identical to sequences characteristic for AAV-Rh74 (see, e.g., VP1, VP2, VP3 of FIGS. 3A-3B). As used herein, an "AAV vector related to AAV-Rh74" and grammatical variations thereof refers to one or more AAV proteins (e.g., VP1, VP2, and/or VP3 sequences) that has substantial sequence identity to one or more polynucleotides or polypeptide sequences that comprise AAV-Rh74. Such AAV vectors related to AAV-Rh74 can therefore have one or more distinct sequences from AAV-Rh74, but can exhibit substantial sequence identity to one or more genes and/or have one or more functional characteristics of AAV-Rh74 (e.g., such as cell/tissue tropism). Exemplary AAV-Rh74 sequences include VP1, VP2, and/or VP3 set forth in FIGS. 3A-3B. In one non-limiting exemplary embodiment, an AAV vector related to AAV-Rh74 has a polynucleotide, polypeptide or subsequence thereof that includes or consists of a sequence at least 80% or more (e.g., 85%, 90%, 95%, 96%, 97%, 98%, 99%, 99.5%, etc.) identical to one or more AAV-Rh74 VP1, VP2, and/or VP3 sequences set forth in FIGS. 3A-3B.

In accordance with the invention, methods and uses include AAV-Rh74 sequences (polypeptides and nucleotides) and subsequences thereof that exhibit less than 100% sequence identity to a reference AAV-Rh74 gene or protein sequence (e.g., VP1, VP2, and/or VP3 sequences set forth in FIGS. 3A-3B), but are distinct from and not identical to known AAV genes or proteins, such as AAV1-AAV11, AAV-Rh10, genes or proteins, etc. In one embodiment, an AAV-Rh74 polypeptide or subsequence thereof includes or consists of a sequence at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical to any reference AAV-Rh74 sequence or subsequence thereof (e.g., VP1, VP2 and/or VP3 sequences set forth in FIGS. 3A-3B).

AAV vectors, including AAV-Rh74, and AAV-Rh74 related vectors, can be constructed using recombinant techniques that are known to the skilled artisan, to include one or more heterologous polynucleotide sequences flanked with functional AAV ITRs. Incorporation of a heterologous polynucleotide defines the AAV as a recombinant vector, or an "rAAV vector." Such vectors can have one or more of the wild type AAV genes deleted in whole or in part, for example, a rep and/or cap gene, but retain at least one functional flanking ITR sequence, as necessary for the rescue, replication, and packaging of the AAV particle. Thus, an AAV vector includes sequences required in cis for viral replication and packaging (e.g., functional ITRs).

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA, small or short interfering (si)RNA, trans-splicing RNA, or antisense RNA). Polynucleotides include naturally occurring, synthetic, and intentionally altered or modified polynucleotides as well as analogues and derivatives. Polynucleotides can be single, double, or triplex, linear or circular, and can be of any length.

A "heterologous" polynucleotide merely refers to a polynucleotide inserted into AAV for purposes of AAV mediated transfer/delivery of the polynucleotide into a cell. Heterologous polynucleotides are typically distinct from AAV nucleic acid. Once transferred/delivered into the cell, a heterologous polynucleotide, contained within the rAAV virion, can be expressed (e.g., transcribed, and translated if appropriate). Alternatively, a transferred/delivered heterologous polynucleotide in a cell, contained within the rAAV virion, need not be expressed. Although the term "heterologous" is not always used herein in reference to polynucleotides, reference to a polynucleotide even in the absence of the modifier "heterologous" includes heterologous polynucleotides in spite of the omission.

The "polypeptides," "proteins" and "peptides" encoded by the "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of the invention, such polypeptides, proteins and peptides encoded by the polynucleotide sequences can be but are not required to be identical to the endogenous protein that is defective, or whose expression is insufficient, or deficient in the treated mammal.

Invention adeno-associated virus (AAV) serotype AAV-Rh74, and related AAV vectors can be used to introduce/deliver polynucleotides stably or transiently into cells and progeny thereof. The term "transgene" is used to conveniently refer to such a heterologous polynucleotide that has been introduced into a cell or organism. Transgenes include any polynucleotide, such as a gene that encodes a polypeptide or protein, a polynucleotide that is transcribed into an inhibitory polynucleotide, or a polynucleotide that is not transcribed (e.g., lacks a expression control element, such as a promoter that drives transcription). For example, in a cell having a transgene, the transgene has been introduced/transferred by AAV "transformation" of the cell. A cell or progeny thereof into which the transgene has been introduced is referred to as a "transformed cell" or "transformant." Typically, a transgene is included in progeny of the transformant or becomes a part of the organism that develops from the cell. Accordingly, a "transformed" or "transfected" cell (e.g., in a mammal, such as a cell or tissue or organ cell), means a genetic change in a cell following incorporation of an exogenous molecule, for example, a polynucleotide or protein (e.g., a transgene) into the cell. Thus, a "transfected" or "transformed" cell is a cell into which, or a progeny thereof in which an exogenous molecule has been introduced, for example. The cell(s) can be propagated and the introduced protein expressed, or nucleic acid transcribed.

Particular non-limiting examples of polynucleotides encoding gene products (proteins) which are useful in accordance with the invention include, but are not limited to: genes that comprise or encode CFTR (cystic fibrosis transmembrane regulator protein), a blood coagulation (clotting) factor (Factor XIII, Factor IX, Factor X, Factor VIII, Factor VIIa, protein C etc.) including gain of function blood coagulation factors, an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g, that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes

[de Groot et al., *Blood* 2008 Oct. 15; 112(8):3303], or hCDR1 [Sharabi et al., *Proc Natl Acad Sci USA*. 2006 Jun. 6; 103(23):8810-5], insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

All mammalian and non-mammalian forms of polynucleotides encoding gene products, including the non-limiting genes and proteins disclosed herein are expressly included, either known or unknown. Thus, the invention includes genes and proteins from non-mammals, mammals other than humans, and humans, which genes and proteins function in a substantially similar manner to the human genes and proteins described herein. A non-limiting example of non-mammalian gene is a Fok nuclease domain, which is bacterial in origin. Non-limiting examples of mammalian non-human FIX sequences are described in Yoshitake et al., 1985, supra; Kurachi et al., 1995, supra; Jallat et al., 1990, supra; Kurachi et al., 1982, Proc. Natl. Acad. Sci. USA 79:6461-6464; Jaye et al., 1983, Nucl. Acids Res. 11:2325-2335; Anson et al., 1984, EMBO J. 3: 1053-1060; Wu et al., 1990, Gene 86:275-278; Evans et al., *Proc Natl Acad Sci USA* 86:10095 (1989), Blood 74:207-212; Pendurthi et al., 1992, Thromb. Res. 65:177-186; Sakar et al., 1990, Genomics 1990, 6:133-143; and, Katayama et al., 1979, Proc. Natl. Acad. Sci. USA 76:4990-4994.

Polynucleotides, polypeptides and subsequences thereof include modified and variant forms. As used herein, the terms "modify" or "variant" and grammatical variations thereof, mean that a polynucleotide, polypeptide or subsequence thereof deviates from a reference sequence. Modified and variant sequences may therefore have substantially the same, greater or less activity or function than a reference sequence, but at least retain partial activity or function of the reference sequence.

Accordingly, the invention also includes naturally and non-naturally occurring variants. Such variants include gain and loss of function variants. For example, wild type human FIX DNA sequences, which protein variants or mutants retain activity, or are therapeutically effective, or are comparably or even more therapeutically active than invariant human FIX in the methods and uses of the invention. In a particular example, collagen IV serves to trap FIX, meaning that when introduced into the muscle tissue of a mammal some of the FIX is not available for participation in blood coagulation because it is retained in the interstitial spaces in the muscle tissue. A mutation in the sequence of FIX that results in a protein with reduced binding to collagen IV (e.g., loss of function) is a mutant useful in the methods of the invention, for example, for treatment of hemophilia. An example of such a mutant human FIX gene encodes a human FIX protein with the amino acid alanine in place of lysine in the fifth amino acid position from the beginning of the mature protein.

Non-limiting examples of modifications include one or more amino acid substitutions (e.g., 1-3, 3-5, 5-10, 10-15, 15-20, 20-25, 25-30, 30-40, 40-50, or more residues), additions (e.g., insertions or 1-3, 3-5, 5-10, 10-15, 15-20, 20-25, 25-30, 30-40, 40-50, or more residues) and deletions (e.g., subsequences or fragments) of a reference sequence. In particular embodiments, a modified or variant sequence retains at least part of a function or an activity of unmodified sequence. Such modified forms and variants can have less than, the same, or greater, but at least a part of, a function or activity of a reference sequence, for example, as described herein.

A variant can have one or more non-conservative or a conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

Accordingly, the invention includes gene and protein variants (e.g., of polynucleotides encoding proteins described herein) which retain one or more biological activities (e.g., function in blood clotting, etc.). Such variants of proteins or polypeptides include proteins or polypeptides which have been or may be modified using recombinant DNA technology such that the protein or polypeptide possesses altered or additional properties, for example, variants conferring enhanced protein stability in plasma or enhanced activity of the protein. Variants can differ from a reference sequence, such as naturally occurring polynucleotides, proteins or peptides.

At the nucleotide sequence level, a naturally and non-naturally occurring variant gene will typically be at least about 50% identical, more typically about 70% identical, even more typically about 80% identical (90% or more identity) to the reference gene. At the amino acid sequence level, a naturally and non-naturally occurring variant protein will typically be at least about 70% identical, more typically about 80% identical, even more typically about 90% or more identity to the reference protein, although substantial regions of non-identity are permitted in non-conserved regions (e.g., less, than 70% identical, such as less than 60%, 50% or even 40%). In other embodiments, the sequences have at least 60%, 70%, 75% or more identity (e.g., 80%, 85% 90%, 95%, 96%, 97%, 98%, 99% or more identity) to a reference sequence. Procedures for the introduction of nucleotide and amino acid changes in a polynucleotide, protein or polypeptide are known to the skilled artisan (see, e.g., Sambrook et al. (1989)).

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence The identity can extend over the entire sequence length or a portion of the sequence. In particular aspects, the length of the sequence sharing the percent identity is 2, 3, 4, 5 or more contiguous polynucleotide or amino acids, e.g., 6, 7, 8, 9, 10, 11, 12, 13, 14, 15, 16, 17, 18, 19, 20, etc. contiguous amino acids. In additional particular aspects, the length of the sequence sharing identity is 20 or more contiguous polynucleotide or amino acids, e.g., 20, 21, 22, 23, 24, 25, 26, 27, 28, 29, 30, 31, 32, 33, 34, 35, etc. contiguous amino acids. In further particular aspects, the length of the sequence sharing identity is 35 or more contiguous polynucleotide or amino acids, e.g., 35, 36, 37, 38, 39, 40, 41, 42, 43, 44, 45, 45, 47, 48, 49, 50, etc., contiguous amino acids. In yet further particular aspects, the length of the sequence sharing identity is 50 or more contiguous polynucleotide or amino acids, e.g., 50-55, 55-60, 60-65, 65-70, 70-75, 75-80, 80-85, 85-90, 90-95, 100-110, etc. contiguous polynucleotide or amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and mathematical algorithm. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Polynucleotides include additions and insertions, for example, heterologous domains. An addition (e.g., heterologous domain) can be a covalent or non-covalent attachment of any type of molecule to a composition. Typically additions and insertions (e.g., a heterologous domain) confer a complementary or a distinct function or activity.

Additions and insertions include chimeric and fusion sequences, which is a polynucleotide or protein sequence having one or more molecules not normally present in a reference native (wild type) sequence covalently attached to the sequence. The terms "fusion" or "chimeric" and grammatical variations thereof, when used in reference to a molecule means that a portions or part of the molecule contains a different entity distinct (heterologous) from the molecule as they do not typically exist together in nature. That is, for example, one portion of the fusion or chimera, includes or consists of a portion that does not exist together in nature, and is structurally distinct.

As set forth herein, polynucleotide sequences include inhibitory and antisense nucleic acid sequences. Inhibitory, antisense, miRNA, shRNA, and RNAi nucleic acids can modulate expression of a target gene. Antisense includes single, double or triple stranded polynucleotides and peptide nucleic acids (PNAs) that bind RNA transcript or DNA (e.g., genomic DNA). Oligonucleotides derived from the transcription initiation site of a target gene, e.g., between positions −10 and +10 from the start site, are another particular example. Triplex forming antisense can bind to double strand DNA thereby inhibiting transcription of the gene. "RNAi" is the use of single or double stranded RNA sequences for inhibiting gene expression (see, e.g., Kennerdell et al., *Cell* 95:1017 (1998); and Fire et al., *Nature,* 391:806 (1998)). Double stranded RNA sequences from a target gene coding region may therefore be used to inhibit or prevent gene expression/transcription in accordance with the methods and uses of the invention. Antisense and RNAi can be produced based upon nucleic acids encoding target gene sequences (e.g., HTT), such as nucleic acid encoding mammalian and human HTT. For example, a single or double stranded nucleic acid (e.g., RNA) can target HTT transcript (e.g., mRNA).

Particular non-limiting examples of genes (e.g., genomic DNA) or transcript of a pathogenic gene (e.e.g, RNA or mRNA) that may be targeted with inhibitory nucleic acid sequences in accordance with the invention include, but are not limited to: pathogenic genes associated with polynucleotide repeat diseases such as huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, Ca v 2.1 P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular oedma (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; or mutant rhodopsin gene (RHO) in autosomal dominantly inherited retinitis pigmentosa (adRP).

As used herein, the term "recombinant," as a modifier of AAV, such as recombinant AAV-Rh74 and related AAV vectors, as well as a modifier of sequences such as recombinant polynucleotides and polypeptides, means that the compositions have been manipulated (i.e., engineered) in a fashion that generally does not occur in nature. A particular example of a recombinant AAV would be where a polynucleotide that is not normally present in the wild-type AAV is within the AAV particle and/or genome. For example, a particular example of a recombinant polynucleotide would be where a polynucleotide (e.g., gene) encoding a protein is cloned into a vector, with or without 5', 3' and/or intron regions that the gene is normally associated within the AAV genome. Although the term "recombinant" is not always used herein in reference to AAV, such as AAV-Rh74 and related AAV vectors, as well as sequences such as polynucleotides and polypeptides, recombinant forms of AAV, AAV-Rh74 and related AAV vectors, and sequences including polynucleotides and polypeptides, are expressly included in spite of any such omission.

Polynucleotide sequences in accordance with the invention can be inserted into a vector. The term "vector" refers to a plasmid, virus (e.g., AAV) or other vehicle that can be manipulated by insertion or incorporation of a polynucleotide. Such vectors can be used for genetic manipulation (i.e., "cloning vectors"), to introduce/transfer polynucleotides into cells, and to transcribe or translate the inserted polynucleotide in cells. A vector generally contains at least an origin of replication for propagation in a cell and expression control element (e.g., a promoter). Control elements, including expression control elements as set forth herein, present within a vector are included to facilitate proper transcription and if appropriate translation (e.g., splicing signal for introns, maintenance of the correct reading frame of the gene to permit in-frame translation of mRNA and, stop codons etc.).

Vectors including AAV-Rh74 and related AAV vectors of the invention can include one or more "expression control elements." Typically, expression control elements are nucleic acid sequence(s), such as promoters and enhancers, that influence expression of an operably linked polynucleotide. Such elements typically act in cis but may also act in trans.

Expression control can be effected at the level of transcription, translation, splicing, message stability, etc. Typically, an expression control element that modulates transcription is juxtaposed near the 5' end of the transcribed polynucleotide (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, 5000 to 10,000 or more nucleotides from the polynucleotide), even at considerable distances. Nevertheless, owing to the polynucleotide length limitations, for AAV-Rh74 and related AAV vectors, such expression control elements will typically be within 1 to 1000 nucleotides from the polynucleotide.

Functionally, expression of the operably linked polynucleotide is at least in part controllable by the element (e.g., promoter) such that the element modulates transcription of the polynucleotide and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

Expression control elements and promoters include those active in a particular tissue or cell type, referred to herein as a "tissue-specific expression control elements/promoters." Tissue-specific expression control elements are typically active in specific cell or tissue (e.g., liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/ enhancer sequences and the other viral promoters/enhancers active in a variety of mammalian cell types, or synthetic elements that are not present in nature.

Expression control elements also can confer expression in a manner that is regulatable, that is, a signal or stimuli increases or decreases expression of the operably linked polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. A regulatable element that decreases expression of the operably linked polynucleotide in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

As used herein, the term "operable linkage" or "operably linked" refers to a physical or functional juxtaposition of the components so described as to permit them to function in their intended manner. In the example of an expression control element in operable linkage with a polynucleotide, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Vectors including AAV-Rh74 and related AAV vectors of the invention can include still additional nucleic acid elements. These elements include, without limitation one or more copies of an AAV ITR sequence, a promoter/enhancer element, a transcription termination signal, 5' or 3' untranslated regions (e.g., polyadenylation sequences) which flank a polynucleotide sequence, or all or a portion of intron I. Such elements also optionally include a transcription termination signal. A particular non-limiting example of a transcription termination signal is the SV40 transcription termination signal.

Inclusion of an intron element may enhance expression compared with expression in the absence of the intron element (Kurachi et al., 1995, supra). AAV vectors typically accept inserts of DNA having a defined size range which is generally about 4 kb to about 5.2 kb, or slightly more. Thus, for shorter sequences, it may be necessary to include additional nucleic acid in the insert fragment in order to achieve the required length which is acceptable for the AAV vector. Introns and intron fragments (e.g. portion of intron I of FIX) fulfill this requirement while also enhancing expression. Thus, the invention is not limited to the inclusion of intron I sequences in the AAV vector, and include other introns or other DNA sequences in place of portions of intron I. Accordingly, other 5' and 3' untranslated regions of nucleic acid may be used in place of those recited for human FIX, particularly when polynucleotides encoding proteins other than human FIX are used in the AAV-Rh74 and related AAV vectors of the invention.

A "portion of intron I" as used herein, is meant region of intron I having a nucleotide length of from about 0.1 kb to about 1.7 kb, which region enhances expression of FIX, typically by about 1.5-fold or more on a plasmid or viral vector template when compared with expression of FIX in the absence of a portion of intron I. A more specific portion is a 1.3 kb portion of intron 1.

Polynucleotides and polypeptides including modified forms can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Polynucleotides and polypeptides including modified forms can also be produced by chemical synthesis using methods known in the art, for example, an automated synthesis apparatus (see, e.g., Applied Biosystems, Foster City, CA). Peptides can be synthesized, whole or in part, using chemical methods (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, PA). Peptide synthesis can be performed using various solid phase techniques (see, e.g., Roberge *Science* 269:202 (1995); Merrifield, *Methods Enzymol.* 289:3 (1997)) and automated synthesis may be achieved, e.g., using the ABI 431A Peptide Synthesizer (Perkin Elmer) in accordance with the manufacturer's instructions.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

In accordance with the invention, treatment methods and uses are provided that include therapeutic methods and uses. Methods and uses of the invention are broadly applicable to diseases amenable to treatment by introducing a gene encoding a protein, or increasing or stimulating gene expression or function, e.g., gene addition or replacement. Methods and uses of the invention are also broadly applicable to diseases amenable to treatment by reducing or decreasing gene expression or function, e.g., gene knockout or reduction of gene expression.

Non-limiting particular examples of diseases treatable in accordance with the invention include those set forth herein as well as a lung disease (e.g., cystic fibrosis), a blood coagulation or bleeding disorder (e.g., hemophilia A or hemophilia B with or without inhibitors), thalassemia, a blood disorder (e.g., anemia), Alzheimer's disease, Parkinson's disease, Huntington's disease, amyotrophic lateral sclerosis (ALS), epilepsy, lysosomal storage diseases, a copper or iron accumulation disorders (e.g., Wilson's or Menkes disease) lysosomal acid lipase deficiency, a neurological or neurodegenerative disorder, cancer, type 1 or type 2 diabetes, Gaucher's disease, Hurler's disease, adenosine deaminase deficiency, a metabolic defect (e.g., glycogen storage diseases), a retinal degenerative disease (such as RPE65 deficiency, choroideremia, and other diseases of the eye), and a disease of a solid organ (e.g., brain, liver, kidney, heart).

Thus, in one embodiment, a method of the invention includes: (a) providing adeno-associated virus (AAV) vector, said vector comprising a heterologous polynucleotide encoding a protein, wherein the heterologous polynucleotide sequence is operably linked to an expression control element conferring transcription of said polynucleotide sequence; and (b) administering an amount of the AAV vector to the mammal wherein said protein is expressed in the mammal. In particular aspects, expression of the protein provides a therapeutic benefit to the mammal.

Methods of the invention include treatment methods, which result in any therapeutic or beneficial effect. In various methods embodiments, an methods of the invention further include inhibiting, decreasing or reducing one or more adverse (e.g., physical) symptoms, disorders, illnesses, diseases or complications caused by or associated with the disease, such as reduced blood clotting time, reduced administration dosage of supplemental clotting factor protein.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Compositions, methods and uses of the invention, can be administered in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

The AAV vector dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the AAV vector, a host immune response to the heterologous polynucleotide or expression product (protein), and the stability of the protein expressed. One skilled in the art can readily determine a AAV virion dose range to treat a patient having a particular disease or disorder based on the aforementioned factors, as well as other factors. Generally, doses will range from at least $1\times10^8$, or more, for example, $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect.

Using hemophilia as an example, generally speaking, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than 5% of normal is needed. With respect to treating such a hemophilic subject, a typical dose is at least $1\times10^{10}$ vector genomes (vg) per kilogram (vg/kg) of the weight of the subject, or between about $1\times10^{10}$ to $1\times10^{11}$ vg/kg of the weight of the subject, or between about $1\times10^{11}$ to $1\times10^{12}$ vg/kg of the weight of the subject, or between about $1\times10^{12}$ to $1\times10^{13}$ vg/kg of the weight of the subject, to achieve a desired therapeutic effect.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal, of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods.

Invention methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease.

The compound, agent, drug, treatment or other therapeutic regimen or protocol can be administered as a combination composition, or administered separately, such as concurrently or in series or sequentially (prior to or following) an AAV vector of the invention. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of an AAV vector of the invention, to a subject. Specific non-limiting examples of combination embodiments therefore include the foregoing or other compound, agent, drug, therapeutic regimen, treatment protocol, process, remedy or composition.

Methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Subjects include animal disease models, for example, mouse and other animal models of blood clotting diseases and others known to those of skill in the art.

Subjects appropriate for treatment in accordance with the invention include those having or at risk of producing an insufficient amount or having a deficiency in a functional gene product (protein), or produce an aberrant, partially functional or non-functional gene product (protein), which can lead to disease. Subjects appropriate for treatment in accordance with the invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease. Target subjects therefore include subjects that have such defects regardless of the disease type, timing or degree of onset, progression, severity, frequency, or type or duration of the symptoms.

Subjects appropriate for treatment in accordance with the invention also include those having or at risk of producing antibodies against AAV. AAV vectors can be administered or delivered to such subjects using several techniques. For example, empty capsid AAV (i.e., AAV lacking a heterologous polynucleotide) can be delivered to bind to the AAV antibodies thereby allowing the AAV vector bearing the heterologous polynucleotide to transform cells of the subject. Amounts of empty capsid AAV to administer can be calibrated based upon the amount of AAV antibodies produced in a particular subject. Alternatively or in addition to, AAV vector can be delivered by direct intramuscular injection (e.g., one or more slow-twitch fibers of a muscle). In another alternative, a catheter introduced into the femoral artery can be used to delivery AAV vectors to liver via the hepatic artery. Non-surgical means can also be employed, such as endoscopic retrograde cholangiopancreatography (ERCP), to deliver AAV vectors directly to the liver, thereby bypassing the bloodstream and AAV antibodies. Other ductal systems, such as the ducts of the submandibular gland, can also be used as portals for delivering AAV vectors into a subject with preexisting anti-AAV antibodies.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for invention methods and uses, but the subject may not manifest the disease. Such subjects therefore include those screened positive for an insufficient amount or a deficiency in a functional gene product (protein), or produce an aberrant, partially functional or non-functional gene product (protein), which can lead to disease; and subjects that screen positive for an aberrant, or defective (mutant) gene product (protein) that leads to disease, even though such subjects do not manifest symptoms of the disease.

Methods and uses of the invention include delivery and administration systemically, regionally or locally, or by any route, for example, by injection, infusion, orally (e.g., ingestion or inhalation), or topically (e.g., transdermally) Such delivery and administration include intravenously, intramuscularly, intraperitoneally, intradermally, subcutaneously, intracavity, intracranially, transdermally (topical), parenterally, e.g. transmucosally or rectally. Exemplary administration and delivery routes include intravenous (i.v.), intraperitoneal (i.p.), intrarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, intralymphatic.

Doses for delivery and administration can be based upon current existing protocols, empirically determined, using animal disease models or optionally in human clinical trials. Initial study doses can be based upon animal studies set forth herein, for a mouse or dog, for example.

Doses can vary and depend upon whether the treatment is prophylactic or therapeutic, the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

AAV vectors and other compositions, agents, drugs, biologics (proteins) can be incorporated into pharmaceutical compositions, e.g., a pharmaceutically acceptable carrier or excipient. Such pharmaceutical compositions are useful for, among other things, administration and delivery to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical formulations and delivery systems appropriate for the compositions and methods of the invention are known in the art (see, e.g., *Remington: The Science and Practice of Pharmacy* (2003) $20^{th}$ ed., Mack Publishing Co., Easton, PA; *Remington's Pharmaceutical Sciences* (1990) $18^{th}$ ed., Mack Publishing Co., Easton, PA; *The Merck Index* (1996) $12^{th}$ ed., Merck Publishing Group, Whitehouse, NJ; *Pharmaceutical Principles of Solid Dosage Forms* (1993), Technonic Publishing Co., Inc., Lancaster, Pa.; Ansel and Stoklosa, *Pharmaceutical Calculations* (2001) $11^{th}$ ed., Lippincott Williams & Wilkins, Baltimore, MD; and Poznansky et al., *Drug Delivery Systems* (1980), R. L. Juliano, ed., Oxford, N.Y., pp. 253-315).

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Pharmaceutical formulations can be packaged in single or multiple unit dosage form for ease of administration and uniformity of dosage.

The invention provides kits with packaging material and one or more components therein. A kit typically includes a label or packaging insert including a description of the components or instructions for use in vitro, in vivo, or ex vivo, of the components therein. A kit can contain a collection of such components, e.g., an AAV vector and optionally a second active, such as another compound, agent, drug or composition.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., compound structures) are an example of a genus of equivalent or similar features.

As used herein, the singular forms "a", "and," and "the" include plural referents unless the context clearly indicates otherwise. Thus, for example, reference to "a polynucleotide" includes a plurality of such polynucleotides, such as a plurality of genes.

As used herein, all numerical values or numerical ranges include integers within such ranges and fractions of the values or the integers within ranges unless the context clearly indicates otherwise. Thus, to illustrate, reference to at least 90% identity, includes 91%, 92%, 93%, 94%, 95%, 95%, 97%, 98%, 99%, etc., as well as 91.1%, 91.2%, 91.3%, 91.4%, 91.5%, etc., 92.1%, 92.2%, 92.3%, 92.4%, 92.5%, etc., and so forth.

Reference to a number with more (greater) or less than includes any number greater or less than the reference number, respectively. Thus, for example, a reference to less than 1,000, includes 999, 998, 997, etc. all the way down to the number one (1); and less than 100, includes 99, 98, 97, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as a percentage range, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-50 therefore includes 1, 2, 3, 4, 5, 6, 7, 8, 9, 10, 11, 12, 13, 14, 15, 16, 17, 18, 19, 20, etc., as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges of 2-72 hours, 2-48 hours, 4-24 hours, 4-18 hours and 6-12 hours, includes ranges of 2-6 hours, 2, 12 hours, 2-18 hours, 2-24 hours, etc., and 4-27 hours, 4-48 hours, 4-6 hours, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

This example includes a description of various materials and methods.

Mice: Male C57BL/6J (WT) mice 8-10 weeks of age, n=5 per experimental group. The dog is a HB dog from the University of North Carolina Chapel Hill colony carrying a missense mutation in the FIX gene (Evans et al., *Proc Natl Acad Sci USA* 86:10095 (1989)).

AAV Vector Constructs: The in vivo studies in mice were performed using a construct expressing human FIX under the control of the ApoE-hAAT liver specific promoter. The study in dogs used a nearly identical promoter and the canine FIX transgene.

Gene Transfer Methodology: All vectors were delivered intravenously. In mice via the tail vein (a volume of 200 microliters per mouse was administered, vector was diluted in PBS). In dogs the vector was delivered via the saphenous vein.

FIX Expression Determination: ELISA was used to measure FIX levels. In mice, the human FIX ELISA antibody pair (capture and secondary) is from Affinity Biologicals. In dogs, an antibody pair also from Affinity Biologicals was used as described in Haurigot et al. (*Mol Ther* 18:1318 (2010)).

Statistical analysis: Statistical analysis was performed with unpaired, two tailed t test. p values <0.05 were considered statistically significant.

AAV Antibody Measurements: An in vitro neutralization assay described in Manno et al., (*Nat Med* 12:342 (2006)) and Mingozzi et al. (*Nat Med* 13:419 (2007)) was used for antibody measurement. In brief, two AAV vector constructs were used in the assay, a single-stranded vector expressing β-galactosidase under the control of the CMV promoter (ssAAV-LacZ), or a self-complementary vector expressing the Renilla reporter gene, AAV-Rh74-CBA-Renilla, under the control of the chicken β-actin promoter (CBA). To increase the efficiency of transduction of AAV vectors in vitro, 2V6.11 cells (ATCC) were used, which expressed the adenoviral gene E4 under the control of an inducible promoter. Cells were seeded in a 96-well plate at a density of $1.25 \times 10^4$ cells/well and a 1:1000 dilution of ponasterone A (Invitrogen) was added to the medium to induce E4 expression. At the day of assay, serial half-log dilutions of heat-inactivated test serum were mixed with medium containing virus. For the ssAAV-LacZ vector, virus concentration used in the assay was $\sim 1 \times 10^{10}$ vg/ml for AAV2 and $\sim 5.5 \times 10^{10}$ vg/ml for AAV5, 6, or 8. For the scAAV-Luc vector, virus concentration in the assay was between −50 and 150-fold lower. Residual activity of the reporter transgene was measured using either a colorimetric assay (ssAAV-LacZ) or a luminometer (scAAV-Luc).

Anti-AAV capsid total IgG or Ig subclasses were measured with a capture assay; ELISA plates were coated with $5 \times 10^{10}$ capsid particles/ml of AAV empty capsids. Plates were blocked with 2% BSA, 0.05% Tween 20 in PBS for 2 hours at room temperature and serial dilutions of samples were loaded onto the wells and incubated overnight at 4° C. Biotin-conjugated anti-human IgG1, IgG2, IgG3, IgG4, or IgM antibody (Sigma) were used as detecting antibodies; streptavidin-HRP was the added for substrate detection. Ig concentration was determined against standard curves made with serial dilution of human purified IgG1, IgG2, IgG3, IgG4, or IgM (Sigma).

AAV Production: The process for vector production is described in detail in Ayuso et al. (*Gene Ther* 17:503 (2010)).

Example 2

This example includes a description of human FIX gene transfer animal (Mice) studies and FIX expression after gene transfer.

C57BL/6 mice (n=5 per group) were injected via the tail vein with AAV vectors bearing the Factor IX (FIX) gene ($2.5^{10}$ vector genomes per mouse) under the control of a liver-specific promoter. Human FIX transgene product (protein) plasma levels in the mice were determined by ELISA at week 1, 2, and 4 post gene transfer, and are illustrated in FIG. 1. AAV-Rh74 showed the highest level of transgene expression in the animals.

Example 3

This example includes a description of animal studies and data demonstrating effective AAV-Rh74 mediated delivery of FIX at therapeutic levels in hemophilia dogs.

Figure 2:
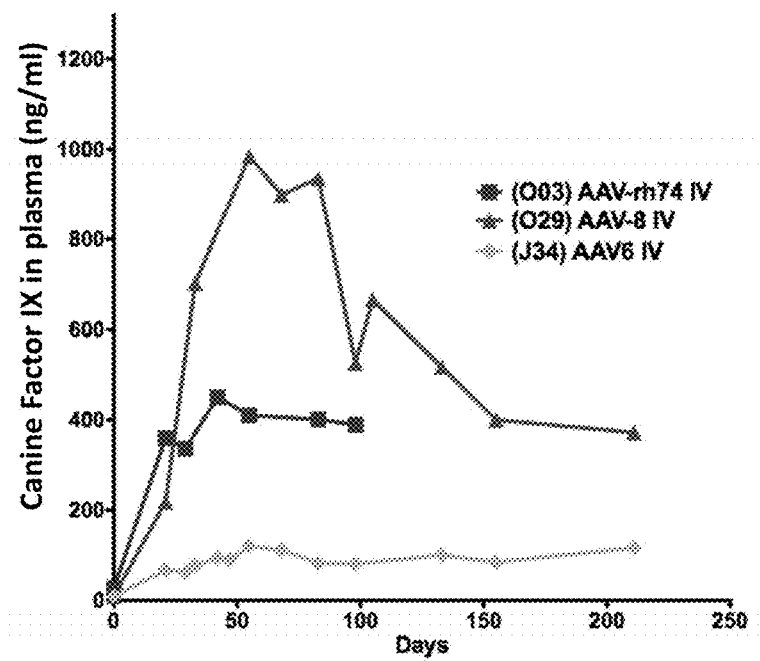
FIG. 2 shows canine FIX plasma levels in hemophilia B dogs after the delivery of $3^{12}$ vector genomes per kilogram (kg) of weight. AAV vectors were infused intravenously (IV) though the saphenous vein and FIX levels were monitored by ELISA. Expression of the therapeutic FIX transgene was driven by a liver specific promoter. AAV8 and AAV-Rh74 vectors performed roughly equally in hemophilia B dogs and were both superior to AAV6.

In brief, hemophilia B dogs were infused intravenously (IV) though the saphenous vein with $3 \times 10^{12}$ vector genomes per kg of weight. Expression of the therapeutic FIX transgene was driven by a liver specific promoter. Vectors and FIX levels were monitored by ELISA. Canine FIX plasma levels are shown in FIG. 2. AAV-Rh74 and AAV8 performed roughly equally in hemophilia B dogs, and both were superior to AAV6.

Example 4

This example includes a description of studies showing the presence of anti-AAV neutralizing antibodies (NAb) in humans.

The data in Table 1 show anti-AAV neutralizing antibodies (NAb) measured in humans with an in vitro assay. Subjects with a NAb titer of 1:1 are defined as naïve or low-titer for anti-AAV antibodies, and are eligible for gene transfer for that AAV serotype (highlighted in grey). AAV-Rh74 exhibited the lowest prevalence of anti-AAV Nab compared to AAV-2 and AAV-8.

TABLE 1

| Subject ID | AAV2 NAb | AAV8 NAb | AAV-Rh74 NAb |
|---|---|---|---|
| GenImm 005 | <1:3.16 | 1:1 | 1:1 |
| GenImm 006 | 1:31.6-1:100 | 1:10-1:31.6 | 1:31.6-1:100 |
| GenImm 015 | 1:3.1-1:10 | 1:1 | 1:1 |
| GenImm 016 | 1:10-1:31.6 | 1:31.6-1:100 | 1:31.6-1:100 |
| GenImm 017 | >1:3160 | >3160 | >1:3160 |
| GenImm 028 | 1:3.1-1:10 | 1:10-1:31.6 | 1:1 |
| GenImm 035 | >1:3160 | 1:100-1:316 | 1:316-1:1000 |
| GenImm 040 | 1:1 | 1:1 | 1:1 |
| GenImm 049 | 1:1 | 1:3.1-1:10 | 1:3.1-1:10 |
| GenImm 053 | 1:3160 | 1:31.6-1:100 | 1:316-1:1000 |
| GenImm 054 | 1:1000-1:3160 | 1:10-1:31.6 | 1:31.6-1:100 |
| GenImm 055 | 1:1000-1:3160 | 1:31.6-1:100 | 1:100-1:316 |
| GenImm 056 | 1:10-1:31.6 | 1:10-1:31.6 | 1:3.1-1:10 |
| GenImm 058 | 1:3.1-1:10 | 1:1 | 1:1 |
| GenImm 060 | >1:3160 | 1:1000-1:3160 | 1:1000-1:3160 |
| GenImm 068 | 1:3160 | 1:316-1:1000 | 1:316-1:1000 |
| GenImm 069 | >1:3160 | >1:3160 | >1:3160 |
| GenImm 070 | 1:10-1:31.6 | 1:1 | 1:1 |
| GenImm 072 | 1:3.1-1:10 | 1:100-1:316 | 1:1 |
| GenImm 074 | 1:3160 | 1:100-1:316 | 1:316-1:1000 |
| GenImm 075 | 1:316-1:1000 | 1:31.6-1:100 | 1:31.6-1:100 |
| GenImm 080 | 1:10-1:31.6 | 1:1 | 1:1 |

TABLE 1-continued

| Subject ID | AAV2 NAb | AAV8 NAb | AAV-Rh74 NAb |
|---|---|---|---|
| GenImm 082 | 1:3.1-1:10 | 1:1 | 1:1 |
| GenImm 083 | 1:1 | 1:1 | 1:1 |
| GenImm 084 | 1:3.1-1:10 | 1:3.1-1:10 | 1:1 |
| GenImm 087 | 1:3.1-1:10 | 1:1 | 1:1 |
| GenImm 088 | | | >1:3160 |
| GenImm 095 | | | 1:1 |
| GenImm 100 | 1:3.1-1:10 | 1:1 | 1:1 |

Example 5

This example includes a description of data showing production amounts of different AAV serotypes including AAV-Rh74.

The data in Table 2 show production yield of different AAV serotypes. Reported are the virus batch size in roller bottles, the total vector yield, and the yield per bottle. All serotypes were packaged with the same expression cassette. AAV-Rh74 has a yield comparable to or greater than the other serotypes evaluated, namely AAV-8, AAV-dj, and AAV-2.

TABLE 2

| Serotype | Batch size (number of roller bottles) | Total vector yield (vector genomes) | Yield per roller bottle (vector genomesi |
|---|---|---|---|
| AAV-Rh74 | 80 | 1.21E+15 | 1.51E+13 |
| AAV-Rh74 | 10 | 1.23E+14 | 1.23E+13 |
| AAV-8 | 30 | 2.54E+14 | 8.47E+12 |
| AAV-dj | 20 | 1.79E+14 | 8.95E+12 |
| AAV-2 | 30 | 1.38E+14 | 4.60E+12 |

Example 6

This example includes a description of data showing that AAVrh74 vector expressing human Factor IX (FIX) under the control of a liver-specific promoter administered to rhesus macaques led to production amounts of FIX in animals, and at higher levels than AAV8 vector administered at the same amount.

In brief, animals were administered either AAV8 or AAVrh74 at a dose of $2 \times 10^{12}$ vector genomes (vg)/kg of weight. Vectors were either formulated in saline or in a mixture of vector and empty AAV capsid (denoted EC).

Figure 4:
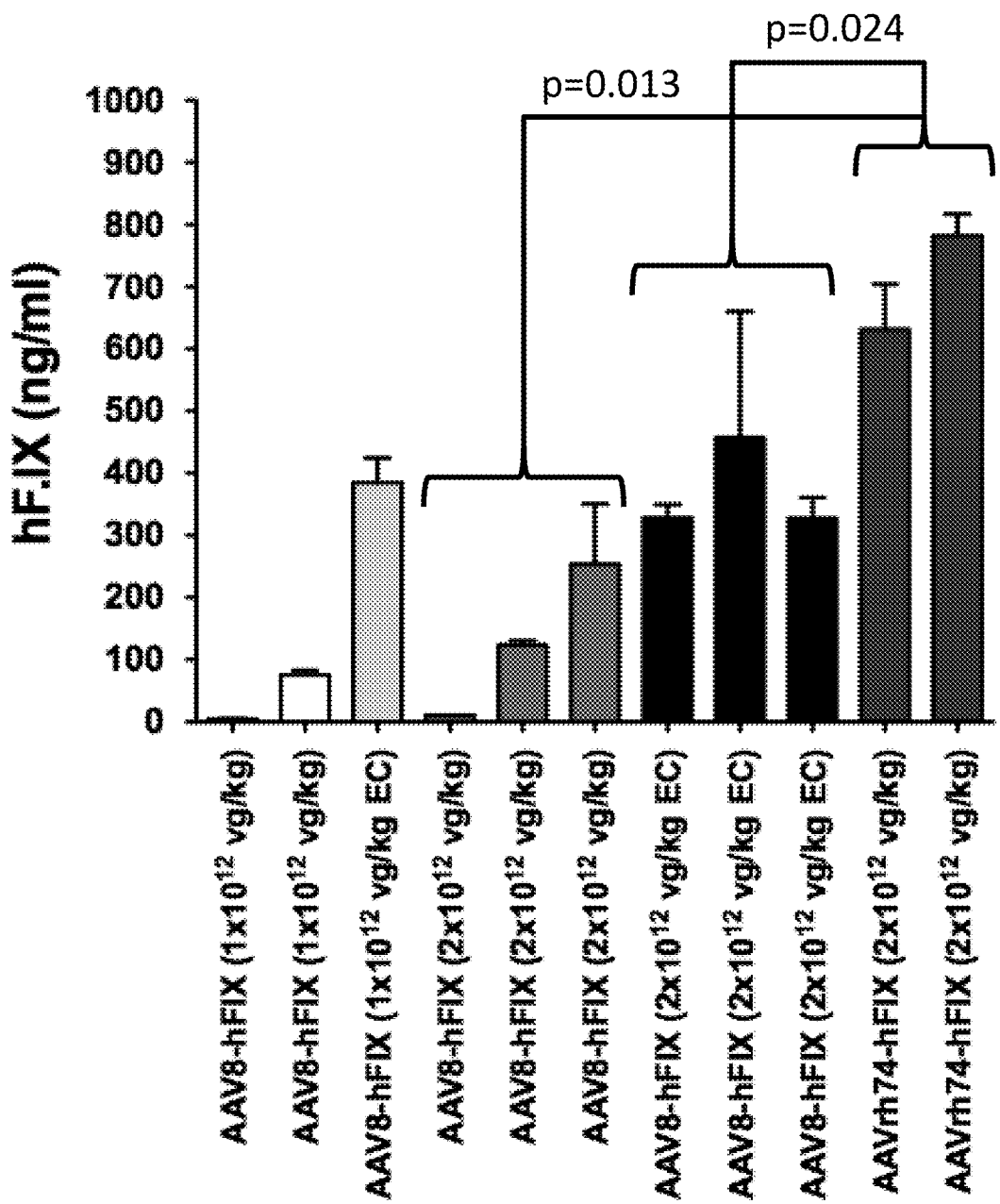
FIG. 4 shows administration of AAV8 and AAVrh74 vector expressing human Factor IX (FIX) (under the control of a liver-specific promoter) to rhesus macaques, a non-human primate, and expression of FIX in the animals. Animals receiving the AAVrh74-FIX vectors (last two bars towards the right margin) expressed the FIX transgene at higher levels compared to the other groups of animals injected at the same dose.

FIG. 4 is a histogram plot of the average (weeks 2 to 8) and standard error or the mean of human FIX measured by an ELISA that detects specifically human FIX in rhesus macaque plasma. Animals receiving the AAVrh74-FIX vector are shown in the last two bars towards the right margin. The data shows that animals receiving the AAVrh74 vectors (last two bars towards right margin) expressed the FIX transgene at higher levels compared to the other groups of animals injected at the same dose (black and grey bars). Average levels were compared using unpaired, two-tailed student t test.

What is claimed:

1. A method for delivering a heterologous polynucleotide sequence into the liver of a mammal, comprising administering an adeno-associated virus (AAV) vector comprising the heterologous polynucleotide sequence which encodes a blood coagulation factor, wherein the heterologous polynucleotide sequence is operably linked to an expression control element, wherein the expression control element is active in liver, and wherein said AAV vector comprises a VP1 sequence comprising the amino acid sequence set forth as SEQ ID NO:1, to said mammal thereby delivering the heterologous polynucleotide sequence encoding the blood coagulation factor into the liver of the mammal.

2. The method of claim 1, wherein said AAV vector comprises a VP2 sequence 100% identical to the amino acid sequence set forth as SEQ ID NO:3.

3. The method of claim 1, wherein said AAV vector comprises a VP3 sequence 100% identical to the amino acid sequence set forth as SEQ ID NO:4.

4. The method of claim 1, wherein said AAV vector comprises a VP2 sequence comprising the amino acid sequence set forth as SEQ ID NO:3 and a VP3 sequence comprising the amino acid sequence set forth as SEQ ID NO:4.

5. The method of claim 1, wherein the mammal produces an insufficient amount of the blood coagulation factor, a defective version of the blood coagulation factor or an aberrant version of the blood coagulation factor.

6. The method of claim 1, wherein the blood coagulation factor encoded by the heterologous polynucleotide sequence is a gain of function version of the blood coagulation factor.

7. The method of claim 1, wherein the mammal has a bleeding disorder.

8. The method of claim 7, wherein the bleeding disorder comprises hemophilia A with or without inhibitors or hemophilia B with or without inhibitors.

9. The method of claim 1, wherein the expression control element comprises a constitutive or a regulatable control element.

10. The method of claim 1, wherein the AAV vector is administered intravenously, intraarterially, intramuscularly, subcutaneously, via catheter, or intra-cavity.

11. The method of claim 1, wherein the mammal is a human.

12. The method of claim 1, wherein the mammal is sero-positive for an AAV1, an AAV2, an AAV3, an AAV4, an AAV5, an AAV6, an AAV7, an AAV8, an AAV9, an AAV10 or an AAV11 serotype.

13. The method of claim 1, wherein the mammal is sero-negative for AAV-Rh74.

14. The method of claim 1, further comprising administering empty capsid AAV.

15. The method of claim 1, wherein a pharmaceutical composition comprises the AAV vector.

16. The method of claim 1, wherein the blood coagulation factor encoded by the heterologous polynucleotide sequence is Factor XIII, Factor IX, Factor X, Factor VIII, Factor VIIa, or protein C.

17. The method of claim 1, wherein the AAV vector is administered intravenously to said mammal.

18. A method of delivering a heterologous polynucleotide encoding a blood coagulation factor to a mammal deficient in said blood coagulation factor expression or function, comprising: (a) providing an AAV vector comprising the heterologous polynucleotide which encodes a blood coagulation factor that can correct for said deficient blood coagulation factor expression or function, wherein the heterologous polynucleotide sequence is operably linked to an expression control element, wherein the expression control element is active in liver and wherein said AAV vector comprises a VP1 sequence comprising the amino acid sequence set forth as SEQ ID NO:1; and (b) administering an amount of the AAV vector results in delivering the heterologous polynucleotide to the mammal, wherein said blood coagulation factor is expressed by a liver cell of the mammal.

19. The method of claim 18, wherein the liver cell is a hepatocyte.

* * * * *

SEQUENCE LISTING

```
<160> NUMBER OF SEQ ID NOS: 4

<210> SEQ ID NO 1
<211> LENGTH: 738
<212> TYPE: PRT
<213> ORGANISM: Adeno-associated virus

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Ser Pro Val Lys Thr Ala Pro Gly Lys Lys Arg
        130                 135                 140
```

```
Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560
```

```
Met Leu Thr Ser Glu Glu Ile Lys Thr Thr Asn Pro Val Ala Thr
                565                 570                 575
Glu Gln Tyr Gly Val Val Ala Asp Asn Leu Gln Gln Asn Ala Ala
            580                 585                 590
Pro Ile Val Gly Ala Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                645                 650                 655
Pro Ala Asp Pro Pro Thr Thr Phe Asn Gln Ala Lys Leu Ala Ser Phe
                660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
        690                 695                 700
Ser Asn Tyr Tyr Lys Ser Thr Asn Val Asp Phe Ala Val Asn Thr Glu
705                 710                 715                 720
Gly Thr Tyr Ser Glu Pro Arg Pro Ile Gly Thr Arg Tyr Leu Thr Arg
                725                 730                 735
Asn Leu

<210> SEQ ID NO 2
<211> LENGTH: 2217
<212> TYPE: DNA
<213> ORGANISM: Adeno-associated virus

<400> SEQUENCE: 2
atggctgccg atggttatct tccagattgg ctcgaggaca acctctctga gggcattcgc    60
gagtggtggg acctgaaacc tggagccccg aaacccaaag ccaaccagca aaagcaggac   120
aacggccggg gtctggtgct tcctggctac aagtacctcg acccttcaa cggactcgac    180
aagggggagc ccgtcaacgc ggcggacgca gcggccctcg agcacgacaa ggcctacgac   240
cagcagctcc aagcgggtga caatccgtac ctgcggtata tcacgccga cgccgagttt   300
caggagcgtc tgcaagaaga tacgtctttt gggggcaacc tcgggcgcgc agtcttccag   360
gccaaaaagc gggttctcga acctctgggc ctggttgaat cgccggttaa gacggctcct   420
ggaaagaaga ccggtagagc catcacccc agcgctctc cagactcctc tacgggcatc   480
ggcaagaaag ccagcagcc cgcaaaaaag agactcaatt ttgggcagac tggcgactca   540
gagtcagtcc ccgaccctca accaatcgga gaaccaccag caggcccctc tggtctggga   600
tctggtacaa tggctgcagg cggtggcgct ccaatggcag acaataacga aggcgccgac   660
ggagtgggta gttcctcagg aaattggcat tgcgattcca catggctggg cgacagagtc   720
atcaccacca gcacccgcac ctgggccctg ccacctaca caaccaccct ctacaagcaa   780
atctccaacg gaacctcggg aggaagcacc aacgacaaca cctacttcgg ctacagcacc   840
ccctgggggt attttgactt caacagattc cactgccact tttcaccacg tgactggcag   900
cgactcatca caacaactg gggattccgg cccaagaggc tcaacttcaa gctcttcaac   960
atccaagtca aggaggtcac gcagaatgaa ggcaccaaga ccatcgccaa taaccttacc  1020
agcacgattc aggtctttac ggactcggaa taccagctcc cgtacgtgct cggctcggcg  1080
```

-continued

```
caccagggct gcctgcctcc gttcccggcg gacgtcttca tgattcctca gtacgggtac    1140
ctgactctga acaatggcag tcaggctgtg ggccggtcgt ccttctactg cctggagtac    1200
tttccttctc aaatgctgag aacgggcaac aactttgaat tcagctacaa cttcgaggac    1260
gtgcccttcc acagcagcta cgcgcacagc cagagcctgg accggctgat gaaccctctc    1320
atcgaccagt acttgtacta cctgtcccgg actcaaagca cgggcggtac tgcaggaact    1380
cagcagttgc tattttctca ggccgggcct aacaacatgt cggctcaggc caagaactgg    1440
ctacccggtc cctgctaccg gcagcaacgc gtctccacga cactgtcgca gaacaacaac    1500
agcaactttg cctggacggg tgccaccaag tatcatctga atggcagaga ctctctggtg    1560
aatcctggcg ttgccatggc tacccacaag gacgacgaag agcgattttt tccatccagc    1620
ggagtcttaa tgtttgggaa cagggagctg gaaaagaca acgtggacta tagcagcgtg    1680
atgctaacca gcgaggaaga aataaagacc accaacccag tggccacaga acagtacggc    1740
gtggtggccg ataacctgca acagcaaaac gccgctccta ttgtaggggc cgtcaatagt    1800
caaggagcct acctggcat ggtgtggcag aaccgggacg tgtacctgca gggtcccatc    1860
tgggccaaga ttcctcatac ggacggcaac tttcatccct cgccgctgat gggaggcttt    1920
ggactgaagc atccgcctcc tcagatcctg attaaaaaca cacctgttcc cgcggatcct    1980
ccgaccacct tcaatcaggc caagctggct tctttcatca cgcagtacag taccggccag    2040
gtcagcgtgg agatcgagtg ggagctgcag aaggagaaca gcaaacgctg gaacccagag    2100
attcagtaca cttccaacta ctacaaatct acaaatgtgg actttgctgt caatactgag    2160
ggtacttatt ccgagcctcg ccccattggc accgttacc tcacccgtaa tctgtaa      2217
```

<210> SEQ ID NO 3
<211> LENGTH: 601
<212> TYPE: PRT
<213> ORGANISM: Adeno-associated virus

<400> SEQUENCE: 3

```
Thr Ala Pro Gly Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Pro Ala Gly Pro Ser Gly Leu Gly Ser
    50                  55                  60

Gly Thr Met Ala Ala Gly Gly Ala Pro Met Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ser Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175
```

```
Leu Asn Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
            195                 200                 205

Phe Thr Asp Ser Glu Tyr Gln Leu Pro Tyr Val Leu Gly Ser Ala His
            210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
                260                 265                 270

Asn Asn Phe Glu Phe Ser Tyr Asn Phe Glu Asp Val Pro Phe His Ser
                275                 280                 285

Ser Tyr Ala His Ser Gln Ser Leu Asp Arg Leu Met Asn Pro Leu Ile
                290                 295                 300

Asp Gln Tyr Leu Tyr Tyr Leu Ser Arg Thr Gln Ser Thr Gly Gly Thr
305                 310                 315                 320

Ala Gly Thr Gln Gln Leu Leu Phe Ser Gln Ala Gly Pro Asn Asn Met
                325                 330                 335

Ser Ala Gln Ala Lys Asn Trp Leu Pro Gly Pro Cys Tyr Arg Gln Gln
                340                 345                 350

Arg Val Ser Thr Thr Leu Ser Gln Asn Asn Asn Ser Asn Phe Ala Trp
                355                 360                 365

Thr Gly Ala Thr Lys Tyr His Leu Asn Gly Arg Asp Ser Leu Val Asn
            370                 375                 380

Pro Gly Val Ala Met Ala Thr His Lys Asp Asp Glu Glu Arg Phe Phe
385                 390                 395                 400

Pro Ser Ser Gly Val Leu Met Phe Gly Lys Gln Gly Ala Gly Lys Asp
                405                 410                 415

Asn Val Asp Tyr Ser Ser Val Met Leu Thr Ser Glu Glu Glu Ile Lys
                420                 425                 430

Thr Thr Asn Pro Val Ala Thr Glu Gln Tyr Gly Val Val Ala Asp Asn
            435                 440                 445

Leu Gln Gln Gln Asn Ala Ala Pro Ile Val Gly Ala Val Asn Ser Gln
            450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Gln Ile
            500                 505                 510

Leu Ile Lys Asn Thr Pro Val Pro Ala Asp Pro Pro Thr Thr Phe Asn
            515                 520                 525

Gln Ala Lys Leu Ala Ser Phe Ile Thr Gln Tyr Ser Thr Gly Gln Val
            530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Asn Val
                565                 570                 575
```

-continued

Asp Phe Ala Val Asn Thr Glu Gly Thr Tyr Ser Glu Pro Arg Pro Ile
               580                 585                 590

Gly Thr Arg Tyr Leu Thr Arg Asn Leu
            595                 600

<210> SEQ ID NO 4
<211> LENGTH: 535
<212> TYPE: PRT
<213> ORGANISM: Adeno-associated virus

<400> SEQUENCE: 4

Met Ala Ala Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
                20                  25                  30

Leu Gly Asp Arg Val Ile Thr Thr Ser Thr Arg Thr Trp Ala Leu Pro
            35                  40                  45

Thr Tyr Asn Asn His Leu Tyr Lys Gln Ile Ser Asn Gly Thr Ser Gly
    50                  55                  60

Gly Ser Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Glu Phe Ser Tyr Asn Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Ser Thr Gly Gly Thr Ala Gly
                245                 250                 255

Thr Gln Gln Leu Leu Phe Ser Gln Ala Gly Pro Asn Asn Met Ser Ala
            260                 265                 270

Gln Ala Lys Asn Trp Leu Pro Gly Pro Cys Tyr Arg Gln Gln Arg Val
        275                 280                 285

Ser Thr Thr Leu Ser Gln Asn Asn Asn Ser Asn Phe Ala Trp Thr Gly
    290                 295                 300

Ala Thr Lys Tyr His Leu Asn Gly Arg Asp Ser Leu Val Asn Pro Gly
305                 310                 315                 320

Val Ala Met Ala Thr His Lys Asp Asp Glu Glu Arg Phe Phe Pro Ser
                325                 330                 335

Ser Gly Val Leu Met Phe Gly Lys Gln Gly Ala Gly Lys Asp Asn Val
            340                 345                 350

-continued

```
Asp Tyr Ser Ser Val Met Leu Thr Ser Glu Glu Glu Ile Lys Thr Thr
            355                 360                 365

Asn Pro Val Ala Thr Glu Gln Tyr Gly Val Val Ala Asp Asn Leu Gln
    370                 375                 380

Gln Gln Asn Ala Ala Pro Ile Val Gly Ala Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
            435                 440                 445

Lys Asn Thr Pro Val Pro Ala Asp Pro Pro Thr Thr Phe Asn Gln Ala
    450                 455                 460

Lys Leu Ala Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Asn Val Asp Phe
            500                 505                 510

Ala Val Asn Thr Glu Gly Thr Tyr Ser Glu Pro Arg Pro Ile Gly Thr
            515                 520                 525

Arg Tyr Leu Thr Arg Asn Leu
530                 535
```